US008653052B2

(12) United States Patent
Gilbert et al.

(10) Patent No.: US 8,653,052 B2
(45) Date of Patent: Feb. 18, 2014

(54) DRUG COMBINATION AND ITS USE IN THE TREATMENT OF MUSCLE LOSS

(75) Inventors: Julian Clive Gilbert, Cambridge (GB); Robert William Gristwood, Cambridge (GB)

(73) Assignee: Acacia Pharma Limited, Cambridge (GB)

( * ) Notice: Subject to any disclaimer, the term of this patent is extended or adjusted under 35 U.S.C. 154(b) by 0 days.

(21) Appl. No.: 12/594,985

(22) PCT Filed: Apr. 24, 2008

(86) PCT No.: PCT/GB2008/001452
§ 371 (c)(1),
(2), (4) Date: Dec. 21, 2009

(87) PCT Pub. No.: WO2008/129308
PCT Pub. Date: Oct. 30, 2008

(65) Prior Publication Data
US 2010/0130456 A1    May 27, 2010

(30) Foreign Application Priority Data

Apr. 24, 2007  (GB) .................................. 0707930.4
Apr. 24, 2007  (GB) .................................. 0707931.2
May 25, 2007  (GB) .................................. 0710101.7

(51) Int. Cl.
*A61K 31/56*        (2006.01)
(52) U.S. Cl.
USPC ...................................................... 514/170
(58) Field of Classification Search
None
See application file for complete search history.

(56) References Cited

U.S. PATENT DOCUMENTS

| 7,101,576 B2 | 9/2006 | Hovey et al. |
| 2007/0149465 A1 | 6/2007 | Kenley et al. |

FOREIGN PATENT DOCUMENTS

| EP | 0 662 324 | 7/1995 |
| EP | 1 818 052 | 8/2007 |
| WO | WO 2006/003222 | 1/2006 |
| WO | WO 2007/095497 | 8/2007 |

OTHER PUBLICATIONS

Weisberg et al, Chest 121:1070-1078, 2002.*
Rossi et al (Chest 121:1058-1069, 2002).*
Muers et al (ERJ 6:729-734, 1993—Abstract only).*
Rennard (Adv Stud Med 3:S408-S415, 2003).*
Busquets et al (Canc Res 64:6725-6731, 2004).*
Schmoll et al (Semin Oncol 18(1 Suppl 2):32-34, 1991—Abstract only).*
Xie et al (Acta Pharmacol Sin 24:277-282, 2003).*
Jatoi et al (J Clin Oncol 20:567-573, 2002).*
Argilés et al., "The Pharmacological Treatment of Cachexia," *Current Drug Targets*, 2004, vol. 5, pp. 265-277.
Busquets et al., "Anticachectic Effects of Formoterol: A Drug for Potential Treatment of Muscle Wasting," *Cancer Research*, Sep. 2004, vol. 64, pp. 6725-6731.
Carbó et al., "Comparative effects of $\beta_2$-adrenergic agonists on muscle waste associated with tumour growth," *Cancer Letters*, 1997, vol. 115, pp. 113-118.
Foradil® Aerolizer®, Formoterol Fumarate Inhalation Powder, Prescribing Information, Rx only, Manufactured by Novartis Pharma AG, Rev: Jun. 2003.
Gomez et al., "Treatment with Megestrol Acetate Improves Human Immunodeficiency Virus-Associated Immune Thrombocytopenia," *Clinical and Diagnostic Laboratory Immunology*, May 2002, vol. 9, pp. 583-587.
Harcourt et al., "Low dose formoterol administration improves muscle function in dystrophic *mdx* mice without increasing fatigue," *Neuromuscular Disorders*, 2007, vol. 17, pp. 47-55.
Kissel etal., "Randomized, double-blind, placebo-controlled trial of albuterol in facioscapulohumeral dystrophy," *Neurology*, 2001, vol. 57, pp. 1434-4440.
Lofdahl etal., "Formoterol fumarate, a new $\beta_2$-adrenoceptor agonist," *Allergy*, 1989, vol. 44, pp. 264-271.
Maltin et al., "Evidence that the hypertrophic action of clenbuterol on denervated rat muscle is not propranolol-sensitive," *Br. J. Pharmacol.*, 1989, vol. 96, pp. 817-822.
Mantovani et al., "Medroxyprogesterone Acetate Reduces the In Vitro Production of Cytokines and Serotonin Involved in Anorexia/cachexia and Emesis by Peripheral Blood Mononuclear Cells of Cancer Patients," *European Journal of Cancer*, 1997, vol. 33, No. 4, pp. 602-607.
Molenaar et al., "Cardiac implications for the use of $\beta_2$-adrenoreceptor agonists for the management of muscle wasting," *British Journal of Pharmacology*, 2006, vol. 147, pp. 583-586.
Rosenborg et al., "Relative systemic dose potency and tolerability of inhaled formoterol and salbutamol in healthy subjects and asthmatics," *Eur J Clin Pharmacol*, 2000, vol. 56, pp. 363-370.
Ryall et al., "Systemic administration of $\beta_2$-adrenoceptor agonists, formoterol and salmeterol, elicit skeletal muscle hypertrophy in rats at micomolar doses," *British Journal of Pharmacology*, Jan. 2006, vol. 147, pp. 587-595.

(Continued)

*Primary Examiner* — Craig Ricci
(74) *Attorney, Agent, or Firm* — Saliwanchik, Lloyd & Eisenschenk

(57) ABSTRACT

The present invention is a product comprising a β2 agonist and a progestin, as a combined preparation for separate, simultaneous or sequential use in the treatment or prevention of muscle loss. The present invention is also a β2 agonist selected from R,R-formoterol, indacaterol or ritodrine, for use in the treatment or prevention of muscle loss.

6 Claims, No Drawings

(56) References Cited

OTHER PUBLICATIONS

Tomiska et al., "Palliative treatment of cancer anorexia with oral suspension of megestrol acetate," *Neoplasma*, 2003, vol. 50, pp. 227-233.

Budzar et al., "Mitomycin-C and Megestrol Acetate in Treatment of Breast Cancer Refractory to Hormonal and Combination Chemotherapy", *Cancer*, 1978, vol. 41, No. 2, pp. 392-395.

McMillan et al., "A prospective randomized study of megestrol acetate and ibuprofen in gastrointestinal cancer patients with weight loss", *British Journal of Cancer*, 1999, vol. 79, No. 3/4, pp. 495-500.

Alexieva-Figusch et al., "Endocrine Effects of the Combination of Megestrol Acetate and Tamoxifen in the Treatment of Metastatic Breast Cancer", *European Journal of Cancer and Clinical Oncology*, 1984, vol. 20, No. 9, pp. 1135-1140.

\* cited by examiner

DRUG COMBINATION AND ITS USE IN THE TREATMENT OF MUSCLE LOSS

This application is a National Stage Application of International Application Number PCT/GB2008/001452, filed Apr. 24, 2008; which claims priority to Great Britain Application No. 0707930.4, filed Apr. 24, 2007; Great Britain Application No. 0707931.2, filed Apr. 24, 2007; and Great Britain Application No. 0710101.7, filed May 25, 2007; all of which are incorporated herein by reference in their entirety.

FIELD OF THE INVENTION

This invention relates to the treatment of diseases and conditions in which a loss of muscle mass occurs.

BACKGROUND TO THE INVENTION

Patients with cancer commonly develop a wasting syndrome termed the anorexia/cachexia syndrome. It increases in prevalence with advancing disease and occurs in more than 80% of patients with advanced cancer. It is an incompletely understood condition that is believed to have multifactorial causality. There are no strict diagnostic criteria but the condition is commonly recognised to include weight loss, anorexia, fatigue/weakness, chronic nausea, decreased performance status and psychological stress from changes in body image. It is refractory to nutritional intervention. The syndrome results in increased morbidity, and is estimated to account for 10%-20% of cancer deaths. Cancer cachexia involves more than just deficiency of calorie intake.

Weight loss that occurs in cancer patients differs from that in starvation, where there is a preferential loss of bodyweight from fat accounting to 75% of the weight loss, the residual occurring from muscle. This is in contrast to cancer patients where weight loss is due equally to fat and muscle. It is thought that a combination of tumour by-products and host cytokine release that occur in cancer cachexia/anorexia combine to produce metabolic abnormalities. In cancer, TNF, IL1, IL6 and interferon gamma are particularly, though not exclusively thought to be involved. In addition the tumour can produce substances which produce cachexia. Significant muscle mass is lost in cachexia but metabolic changes also occur. These include excess lactate production and preferential atrophy of the type 2 muscle fibres which are responsible for high anaerobic glycolytic metabolism.

Current treatments for cancer cachexia include the use of progestational agents, megestrol acetate and medroxyprogesterone acetate, and corticosteroids including dexamethasone, methylprednisolone and prednisolone. Potential treatments include the use of COX-2 inhibitors, for example celecoxib, nimesulide, ketorolac, indomethacin, ibuprofen, etodolac and diclofenac; cannabinoids for example dronabinol; antidepressants such as mirtazapine and olanzapine; cytokine modulators such as thalidomide; pentoxifylline; metabolic inhibitors such as hydrazine sulphate; anabolic agents such as oxandrolone, nandrolone decanoate and fluoxymesterone; angiotensin converting inhibitors; angiotensin II antagonists; and renin inhibitors.

Megestrol acetate has been most studied in the class of progestational agents (progestins). It has been shown to produce a weight gain of greater than 5% in 15% of cancer patients treated and there is evidence that a significant component of the gain is due to fat. Its mechanism of action is unclear and could be related to anabolic glucocorticoid activity, effects on cytokine release, and inhibition of IL1 and IL6 as well as TNF. It has a stimulatory effect on appetite. In several clinical trials megestrol acetate or medroxy-progesterone acetate (MPA) have been found to improve appetite, calorie intake and nutritional status. Megestrol has demonstrated benefit from doses ranging from 160 mg (40 mg orally four times per day) to 1600 mg on appetite, calorie intake, body weight gain (mainly fat) and sensation of well-being, with an optimal dose of 800 mg/day. It is recommended that a patient be started on the lowest dose (160 mg/day) and the dose be titrated upwards, according to the clinical response.

Adverse effects are related to drug dosage. These effects include, also for medroxyprogesterone acetate, thromboembolism, increased peripheral oedema, hypertension, hyperglycaemia, alopecia, Cushing's syndrome, adrenal suppression, and adrenal insufficiency if they are suddenly discontinued. Progestins are recommended for patients with an expected survival time of greater than 4 weeks.

Corticosteroids have marked symptomatic effects and increase appetite, food intake, sensation of well-being and performance status. This effect is however limited to a few weeks. Due to the significant side effects of long-term treatment and their short duration of action for cachexia, they are more appropriately used in patients with a short expected survival time and where weight gain is not an expected outcome.

In addition to cancer cachexia, a severe loss of muscle mass and strength, often in association with loss of fat mass, is associated with a number of other conditions and diseases including dystrophy, sepsis, AIDS, burn injury, chronic obstructive pulmonary disease (COPD) and congestive heart failure (CHF).

It has recently been shown (Busquets et al 2004, Cancer Res 64:6725-6731) that administration of the β2-agonist racemic formoterol to both rats and mice bearing highly cachectic tumors, resulted in a reversal of the muscle-wasting process. The anti-wasting effects of the drug were based on both an activation of the rate of protein synthesis and an inhibition of the rate of muscle proteolysis. Northern blot analysis revealed that formoterol treatment resulted in a decrease in the mRNA content of ubiquitin and proteasome subunits in gastrocnemius muscles; this, together with the decreased proteasome activity observed, suggest that the main anti-proteolytic action of the drug may be based on an inhibition of the ATP-ubiquitin-dependent proteolytic system. Interestingly, formoterol was also able to diminish the increased rate of muscle apoptosis (measured as DNA laddering as well as caspase-3 activity) present in tumor-bearing animals. These authors concluded from their study that formoterol exerted a selective powerful protective action on heart and skeletal muscle by antagonising the enhanced protein degradation that characterises cancer cachexia; in addition, formoterol also had a protective action against the apoptotic effects of skeletal muscle. They also concluded that "conversely to what is found with other β2 agonists that have numerous side effects and considerable toxicity in humans, formoterol could be revealed as a potential therapeutic tool in pathological states wherein muscle protein hypercatabolism is a critical feature, such as cancer cachexia or other wasting diseases."

Ritodrine is currently used to produce uterine relaxation in pregnant women. As reported in U.S. Pat. No. 5,449,694, (−)-ritodrine is the more potent enantiomer.

Indacaterol, also known as QAB-149 or 5-[(R)-2-(5,6-diethylindan-2-ylamino)-1-hydroxyethyl]-8-hydroxy-1H-quinolin-2-one, is an adrenergic β2 agonist. It is a long acting bronchodilator being developed as a potential once daily treatment for asthma and COPD. Administration for these respiratory conditions is conducted using a multidose dry powder inhaler.

SUMMARY OF THE INVENTION

According to a first aspect, the present invention is a product comprising a β2 agonist and a progestin, as a combined preparation for separate, simultaneous or sequential use in the treatment or prevention of muscle loss.

According to a second aspect, the present invention is a product comprising a β2 agonist selected from R,R-formoterol, indacaterol or ritodrine, for use in the treatment or prevention of muscle loss.

DESCRIPTION OF THE INVENTION

As used herein, the term β2 agonist means a β2-adrenoreceptor agonist.

Examples of β2 agonists suitable for use in the invention are albuterol, salmeterol, bitolterol, pirbuterol, formoterol, indacaterol or ritodrine. In a preferred embodiment, the (β2 agonist is formoterol, ritodrine or indacaterol. If the β2 agonist is a chiral molecule, it may be used as a racemate, as a non-racemic mixture or as a substantially single enantiomer. In one embodiment, the β2 agonist is racemic formoterol. In another embodiment, the β2 agonist is R,R-formoterol. In yet another embodiment, the β2 agonist is substantially single enantiomer(−)-ritodrine. In a further embodiment, the β2 agonist is racemic ritodrine.

Each active agent may be used, according to the invention, in any appropriate form, e.g. as a salt, hydrate or prodrug. For example, if R,R-formoterol is used, it may be in the form of a common salt.

As used herein, indacaterol is 5-[(R)-2-(5,6-diethylindan-2-ylamino)-1-hydroxyethyl]-8-hydroxy-1H-quinolin-2-one. Formoterol and ritodrine may be racemic, or may be a substantially single enantiomer. In one embodiment the formoterol is the R,R-enantiomer fumarate salt, i.e. (±)-N-[2-Hydroxy-5-[1(R*)-hydroxy-2-[1(R*)-methyl-2-(4-methoxyphenyl)ethylamino]ethyl]phenyl]formamide fumarate (2:1) monohydrate. In another embodiment, the ritodrine is the S,R-enantiomer hydrochloride salt, i.e. 4-[1(S)-Hydroxy-2(R)-[2-(4-hydroxyphenyl)ethylamino]propyl]phenol hydrochloride. According to the second aspect of the invention, a product comprising a β2 agonist selected from R,R-formoterol, indacaterol or ritodrine, is useful in the treatment or prevention of muscle loss. In one embodiment, that product does not comprise a macrolide. In a preferred embodiment, only when that product comprises ritodrine, the product does not also comprise a macrolide.

Each of the listed β2 agonists may be used independently, or in combination with each other.

Examples of progestins that can be used in the invention are megestrol and medroxy-progesterone acetate (MPA). Preferably, the progestin is megestrol. More preferably, the megestrol is the acetate salt.

According to one aspect, the invention is a product comprising a β2 agonist and a progestin, for use in the treatment or prevention of muscle loss. In a preferred embodiment, that product does not comprise a macrolide. In one embodiment, only when the β2 agonist is formoterol and the progestin in megestrol acetate, the product of the invention does not include a macrolide. In another embodiment, only when the β2 agonist is formoterol or ritodrine, and the progestin is megestrol acetate, the product of the invention does not include a macrolide.

In a further preferred embodiment, only when the β2 agonist is racemic formoterol and the progestin is megestrol acetate, the product of the invention does not include a macrolide (i.e. when the β2 agonist is anything other than racemic formoterol and the progestin is anything other than megestrol acetate, a macrolide may be included in the product of the invention). In another preferred embodiment, only when the β2 agonist is racemic formoterol or racemic ritodrine, and the progestin is megestrol acetate, the product of the invention does not include a macrolide (i.e. when the β2 agonist is anything other than racemic formoterol or racemic ritodrine, and the progestin is anything other than megestrol acetate, a macrolide may be included in the product of the invention).

For the purpose of the present invention, the product is preferably administered by the oral route (this includes buccal and sublingual administration). For the oral route, capsules, tablets including fast dissolving tablets, solutions, suspensions, gums, meltabs or any other oral formulation which one skilled in the art is aware of may be used. Many such types of formulation are known to those skilled in the art and may be used to practise this invention. For example, immediate release and control release tablets may be used to administer a product of the invention.

Alternatively, the product of the invention may be administered by a parenteral route. Immediate release and controlled release injection technologies are available to those skilled in the art and may be used to practise the invention when parenteral delivery is used.

Appropriate dosage levels may be determined by any suitable method known to one skilled in the art. It will be understood, however, that the specific dose level for any particular patient will depend upon a variety of factors including the activity of the specific compound employed, the age, body weight, general health, sex, diet, time of administration, route of administration, rate of excretion, drug combination and the severity of the condition to be treated.

For a product of the invention that comprises more than one active agent. The respective active agents may be formulated together in a single dosage form. Alternatively, they may be formulated separately and packaged together, or they may be administered independently. In certain cases, a patient may be receiving one drug for the treatment of another indication; this invention then comprises administering the other drug.

It may be advantageous to combine or co-administer a product of the invention with other classes of drug. Drugs which may be co-administered with a product of the invention include, but are not limited to, corticosteroids, prokinetic agents, cannabinoids, eicosapentaenoic acid and non-steroidal anti-inflammatory agents. The respective drugs may be administered simultaneously, separately or sequentially.

A product of the invention is useful for the treatment and prevention of muscle loss. Preferably, the loss of muscle occurs in association with a loss of fat mass.

In a preferred embodiment, the muscle loss is in association with cancer cachexia/anorexia. In other embodiments, the muscle loss is associated with one or more conditions selected from COPD, dystrophy, sepsis, AIDS, burn injury, CHF, diabetes, an immobilisation state, aging, liver cirrhosis, renal failure, rheumatoid arthritis, a nutrition disorder, a fatigue condition and Alzheimer's disease.

The following study may provide evidence of the utility of the present invention.

Study

This study involves the use of the Yoshida AH-130 rat ascites hepatoma model, which is a particularly suitable model system for studying the mechanisms involved in the establishment of cachexia. Its growth in the host causes rapid and progressive loss of bodyweight and tissue wasting, particularly in skeletal muscle. This study examines the effects of the β2 agonists racemic formoterol, R,R-formoterol, racemic ritodrine, single enantiomer(−)-ritodrine and indacaterol on tissue wasting caused by the tumour. Co-administration of each of these β2 agonists with the progestin, megestrol acetate, is also investigated.

Wistar rats weighing about 100 g are used (Busquets et al 2004, Cancer Res 64:6725-6731). The animals are maintained on a regular light-dark cycle (light from 08.00 am to 8.00 pm) with free access to food and water. Their diet consists of 54% carbohydrate, 17% protein and 5% fat, and the food intake is measured daily. Rats are given an intraperitoneal inoculum of $10^8$ AH-130 Yoshida ascites hepatoma cells obtained from exponential tumours.

The animals were divided into groups: those receiving the test drugs and those receiving vehicle. Drug administration is by subcutaneous injection. Seven days after tumour transplantation, the animals are weighed and anaesthetised with a ketamine/xylacine mixture. The tumour is harvested from the peritoneal cavity, and its volume and cellularity evaluated. Cells are then separated from the ascetic fluid by centrifugation at 100 g for 10 min. Tissues are rapidly excised, weighed and frozen in liquid nitrogen.

The measurements taken are: initial body weight, final bodyweight, bodyweight increase, carcass weight, total food intake, total water intake, muscle weights including tibialis, EDL, gastrocnemius and soleus, adipose weights including white adipose tissue (dorsal and pregenital) and brown adipose tissue, organ weights including liver, heart, kidneys and spleen, tumour volume and cellularity.

This study is designed to show that racemic formoterol, R,R-formoterol, racemic ritodrine, single enantiomer(−)-ritodrine and indacaterol inhibit loss of skeletal muscle mass caused by the tumour. This should occur with minimal or no increase in heart weight or decrease in food consumption. This study is also designed to show that coadministration of each of the listed β2 agonists with megestrol acetate gives additional benefit by inhibiting the decrease in muscle and/or fat caused by the tumour and in the selectivity of these effects, and by increasing food consumption.

In an initial experiment, the tumour bearing rats were divided into three groups. The first group were untreated; the second group received 10 μg/kg/day of racemic formoterol fumarate; and the third group received a combination of 10 μg/kg/day of racemic formoterol and 100 mg/kg/day of megestrol acetate. The rats were monitored over a 3 day period.

Total food intake for the first (untreated) group at day 3 was 43±1 g/100 g rat (n=10). Total food intake for the second group (racemic formoterol only) at day 3 was 45±2 g/100 g rat (n=9). Total intake for the third group (racemic formoterol plus megestrol acetate) at day 3 was 48±2 g/100 g rat (n=10). The increase in food intake in the animals treated with the combination (third group) was 11.6% and this was statistically significant.

The invention claimed is:

1. A method for the treatment of muscle loss in association with cancer cachexia, wherein said method comprises administering, separately concomitantly, simultaneously or sequentially, to a subject having muscle loss in association with cancer cachexia, a therapeutically effective amount of formoterol and megestrol, wherein said megestrol is administered orally at a dose of 160 mg/day to 1600 mg/day.

2. The method according to claim 1, wherein the megestrol is the acetate salt.

3. The method according to claim 1, wherein formoterol is R,R-formoterol.

4. The method according to claim 1, wherein the formoterol and megestrol are administered orally.

5. The method according to claim 3, wherein the R,R-formoterol and megestrol are administered orally.

6. The method according to claim 1, wherein the subject is a human.

* * * * *

UNITED STATES PATENT AND TRADEMARK OFFICE
CERTIFICATE OF CORRECTION

| | | |
|---|---|---|
| PATENT NO. | : 8,653,052 B2 | Page 1 of 1 |
| APPLICATION NO. | : 12/594985 | |
| DATED | : February 18, 2014 | |
| INVENTOR(S) | : Julian Clive Gilbert et al. | |

It is certified that error appears in the above-identified patent and that said Letters Patent is hereby corrected as shown below:

In the Claims:

Column 6,
Lines 21-22, "wherein said method comprises administering, separately concomitantly, simultaneously or sequentially" should read --"wherein said method comprises administering, concomitantly--.

Signed and Sealed this
Twenty-second Day of July, 2014

Michelle K. Lee
*Deputy Director of the United States Patent and Trademark Office*